(12) United States Patent
Siemens

(10) Patent No.: US 7,440,100 B2
(45) Date of Patent: Oct. 21, 2008

(54) METHOD FOR EVALUATION OF A SCATTERED LIGHT SIGNAL AND SCATTERED LIGHT DETECTOR USED FOR CARRYING OUT SAID METHOD

(75) Inventor: Andreas Siemens, Laatzen (DE)

(73) Assignee: Wagner Alarm Sicherungssysteme GmbH, Langenhagen (DE)

( * ) Notice: Subject to any disclaimer, the term of this patent is extended or adjusted under 35 U.S.C. 154(b) by 80 days.

(21) Appl. No.: 10/582,396

(22) PCT Filed: Dec. 22, 2004

(86) PCT No.: PCT/EP2004/014632

§ 371 (c)(1),
(2), (4) Date: Jun. 12, 2006

(87) PCT Pub. No.: WO2005/071390

PCT Pub. Date: Aug. 4, 2005

(65) Prior Publication Data

US 2007/0139649 A1    Jun. 21, 2007

(30) Foreign Application Priority Data

Jan. 27, 2004  (DE) .................. 10 2004 004 098

(51) Int. Cl.
*G01N 21/00* (2006.01)
(52) U.S. Cl. .................. 356/338; 356/335; 356/338; 356/343
(58) Field of Classification Search .......... 356/335–343
See application file for complete search history.

(56) References Cited

U.S. PATENT DOCUMENTS

| 4,225,791 A |   | 9/1980 | Kompelien |
|---|---|---|---|
| 4,266,219 A |   | 5/1981 | Foster et al. |
| 4,506,161 A |   | 3/1985 | Muggli et al. |
| 5,117,219 A |   | 5/1992 | Tice et al. |
| 5,296,910 A | * | 3/1994 | Cole .......................... 356/28.5 |
| 5,477,218 A |   | 12/1995 | Manmoto et al. |
| 5,831,537 A | * | 11/1998 | Marman ...................... 340/628 |
| 6,184,537 B1 |   | 2/2001 | Knox et al. |
| 6,876,305 B2 | * | 4/2005 | Kadwell et al. ............. 356/338 |

FOREIGN PATENT DOCUMENTS

| EP | 0 576 200 | 12/1993 |
|---|---|---|
| GB | 1 405 615 | 9/1975 |
| GB | 2 034 026 | 5/1980 |
| WO | WO 02/089082 | 11/2002 |
| WO | WO 2004/019294 | 3/2004 |

* cited by examiner

*Primary Examiner*—L.G. Lauchman
*Assistant Examiner*—Iyabo S Alli
(74) *Attorney, Agent, or Firm*—Dennison, Schultz & MacDonald; George H. Spencer

(57) ABSTRACT

A method of evaluating a scattered light signal generated by a scattered light receiver when detecting especially fine particles in a carrier medium, wherein the scattered light signal runs through a filter algorithm operation to evaluate the scattered light signal subject to specific filter algorithms, the filter algorithm operation being based on a slope of the scattered light signal.

18 Claims, 4 Drawing Sheets

METHOD FOR EVALUATION OF A SCATTERED LIGHT SIGNAL AND SCATTERED LIGHT DETECTOR USED FOR CARRYING OUT SAID METHOD

CROSS-REFERENCE TO RELATED APPLICATIONS

This application constitutes the National Stage Entry of the PCT International Patent Application No. PCT/EP2004/014632, filed Dec. 22, 2004, and claims the priority of German Patent Application No. 10 2004 004 098.2, filed Jan. 27, 2004, in the German Patent and Trademark Office, the disclosures of which are incorporated herein by reference.

1. Field of the Invention

An aspect of the present invention relates to a method of evaluating a scattered light signal generated by a scattered light receiver when detecting especially fine particles in a carrier medium.

Another aspect of the present invention relates to a scattered light detector to carry out the above-cited method having a housing, an inlet opening and an outlet opening in said housing, between which the carrier medium flows through the housing on a flow path, having a light source which directs light to a scattered light center lying on the flow path, having a scattered light receiver to receive a portion of the light scattered on particles in the scattered light center, and having a scattered light signal amplifier to amplify the scattered light signal.

2. Description of the Related Art

Methods and devices for evaluating a scattered light signal are known and used especially in scattered light detectors for aspiration fire alarm systems. Generally, they detect solid matter or liquid particles, whereby the carrier medium includes a representative partial quantity of the air of a room to be monitored or the device cooling air of a device to be monitored. In the case of an aspiration fire alarm system, this representative quantity of air is actively suctioned by means of a ventilator and fed into the inlet opening of the scattered light detector. In the case of monitored devices such as EDP equipment, for example, or other similar electronic devices such as measuring, control or regulating devices, it is, in principle, also possible to use the internal flow of the device-cooling air itself to feed a representative partial quantity of the device-cooling air into the inlet opening of the scattered light detector as the carrier medium. In this case, an active suctioning ventilator is then rendered unnecessary.

A description of the operation of scattered light detectors as described above will now be provided. While the carrier medium flows through the scattered light center on a flow path thereof through the housing of the scattered light detector, the light of the light source traverses the scattered light center, and, thus, the carrier medium flowing through it and, provided it is not scattered onto particles in the carrier medium, is absorbed in a light trap opposite thereto. This is the normal and predominantly prevailing operational state. When the ray of light from the light source hits a particle, for example a smoke particle or a smoke aerosol, providing a first indication of a fire in the initial stages, this particle deflects a fraction of the light from its original direction as scattered light. This scattered light is then received by a highly photosensitive receiver, the so-called scattered light receiver, and its intensity is measured by a subsequent evaluation circuit. An alarm is triggered when a specific light intensity threshold is exceeded.

A precise adaptation to environmental variables, special design features, and appropriate signal processing are necessary so that such an optical system works accurately and with high sensitivity. This would entail, for example, changing the sensitivity of the detector based on the scattered light receiver's point of installation. For instance, detector sensitivity needs to be set far higher for clean rooms, in which, for example, computer chips are manufactured, than it does in offices spaces, as even the smallest quantities of dust particles or suspended particles in the air of the former needs to trigger an alarm.

Since the intensity of the light radiated by the detector's light source stands in direct correlation to the temperature, it is likewise necessary to configure temperature monitoring for the detector. It is in fact theoretically necessary, given a rising temperature, to increase the light output of the light source, for example by increasing the operational current. Apart from the high energy costs, however, this leads to a disproportionately shortened operating life, especially in the case of laser diodes. Even if the maximum operational current of an LED is not reached, operation at the maximum upper current limit shortens its lifetime immensely. Generally speaking, configuring a highly-sensitive optical scattered light detector requires precise and adapted signal processing.

Printed publication EP 0 733 894 B1, which relates to adapting the temperature of a photoelectric sensor for detecting fine particles in the air such as, for example, smoke or dust, is provided to this end. The detector disclosed in this publication has a light source and a light-receiver, which produces a sensor output upon detecting a scattering of light that is caused by the presence of fine particles in the light radiated from the light source. The detector thereby includes a controller that controls the quantity of light emitted from the light source based on a reference temperature value. The light source is thereby pulsed switched. If its temperature exceeds a specific threshold, the controller changes the interval between the individual light pulses. This enables an intensified cooling of the light source. This control loop is continued until the highest threshold is exceeded, upon which an alarm signal is then triggered, since the cause can be attributed to either a malfunctioning of the detector or the rise in temperature being due to the rise in the ambient temperature in consequence of a fire.

The disadvantage to this device, however, is that increasing the distance between the respective light pulses increases the detector's dead area, at the expense of accuracy. While this device essentially solves the problem of dependency between temperature and light output of the light source, it indicates no possibility of counteracting the change in detector sensitivity, of calibrating the detector, or evaluating the received scattered light signal according to given specifications.

Calibrating a conventional scattered light detector is customarily done with a reference signal. To properly design, test or demonstrate fire alarm systems, it is known to conduct smoke tests using a procedure which produces smoke aerosols, wherein a test sample is pyrolized by heating. Among other things, these tests thereby serve in determining where the detectors should be arranged within an electronic system or within a room. In order to make a test as realistic as possible, methods for producing smoke aerosols are used, with the help of which a reference value can be created for the smoke in order to test and/or calibrate the smoke detectors to same.

The German DE 4 329 847 C1 printed patent describes a method for producing smoke aerosols to properly design, test or demonstrate the effectiveness of fire alarm systems as well as a pyrolysis device with which this method may be carried out. In the procedure, a test sample, for example an electrical cable or other such similar object, is kept at a constant or virtually constant temperature for a defined interval of time. The device and this associated method thereby work in the so-called pyrolysis phase, in which low-power and invisible smoke aerosols are released. The detection range of modern early warning fire systems lies within this first phase of a developing fire. Depending upon the requirements for detection accuracy, it must also be possible, among other things, to then adapt the scattered light detector to this reference signal.

SUMMARY OF THE INVENTION

Based on the points specified above, the present invention addresses the task of further developing a method for evaluating a scattered light signal to be more effective, more versatile and more exact. The invention furthermore addresses the task of providing a scattered light detector to carry out the above-cited method, its mode of functioning being more precise, more versatile, less prone to errors and less expensive than that of the scattered light detectors known in the art.

Therefore, in accordance with an aspect of the invention, a method of evaluating a scattered light signal generated by a scattered light receiver when detecting especially fine particles in a carrier medium, comprising running the scattered light signal through a filter algorithm operation to evaluate the scattered light signal subject to specific filter algorithms, the filter algorithm operation being based on a slope of the scattered light signal.

Another aspect of the invention is that cycling through various calibrating and compensating operations enables an exact adjustment of the scattered light signal. Depending upon the requirements of the scattered light signal detection, the accuracy and the prevailing environment variables, it is therefore possible to adapt the scattered light detector in such a manner so as to enable a precise and error-free scattered light detection.

In each individual operation, adjustments are made. In a calibration operation, the scattered light detector is calibrated with a reference signal. Among other factors, this adjustment takes the respective environmental conditions into account since a carrier medium can exhibit a different "base level of pollution" in normal operation depending upon site of installation.

In a drift compensation operation, the above-cited calibration is made over a longer period of time, i.e. usually 2 to 3 days. Averaging the chamber value to a tracked chamber value, whereby the chamber value is the scattered light signal to be received by the scattered light detector when there is no smoke or smoke aerosol present in the scattered light center, thereby improves the accuracy of the scattered light detector, since its sensitivity adjustment can be made with due consideration of this average value.

A temperature compensation operation serves in adapting the scattered light detector to the dependent temperature/radiated light output relationship. Allowance is made here for the fact that actual light output emitted by a source of light decreases as temperature increases and vice-versa.

A sensitivity adjusting operation enables the scattered light detector to be adjusted to the necessary stages of sensitivity, as required depending upon detector area of application.

A filter algorithm operation enables the analysis of a scattered light signal subject to specific filter algorithms in order to ensure reliable and accurate alarm output.

A combination of different adapting and calibrating operations results in a detection method which is extremely precise, of versatile applicability and which additionally functions exceptionally accurate. Of course, in order to save costs, it would be conceivable to omit one or the other adapting operations, provided same would not be expressly necessary.

A method for evaluating a scattered light signal wherein the scattered light detector has an integration amplifier as the scattered light signal amplifier, in which the integration time of the integration amplifier is set during the calibration operation such that the scattered light signal corresponds to a reference signal of a reference indicator, constitutes an advantageous improvement with the method specified at the outset. Changing the integration time enables a very economical and readily automated adaptation of the scattered light detector to a reference signal. Among other things, it is also possible to make this adaptation by adjusting the drive current of the light source so as to change the radiated luminous energy which, however, occurs at the expense of the operating life of the light source and requires increased power. With the method according to the invention, the drive current of the light source remains constant.

Different methods can be used to change the sensitivity of a scattered light detector in accordance with the invention. One would be changing the pulse width of the light source drive current. The pulse width refers to the duration of a light pulse. Reducing the pulse width decreases the sensitivity of the scattered light detector, increasing the pulse width raises the sensitivity. The other possibility is changing the integration time of any integration amplifier provided to function as a scattered light signal amplifier. With this method as well, increasing the integration time of the integration amplifier leads to higher sensitivity and reducing the integration time leads to a scattered light detector with less responsiveness. Both methods of changing the sensitivity of a scattered light detector are economical, forestall material damage and allow scattered light detectors to be adapted in an exemplarily simple manner. It is of course possible to change both the integration time as well as the pulse width incrementally or continuously. Incremental here refers to, for example, fixed increments of percentile sensitivities such that the scattered light detector works at 25%, 50%, 75% and 100% sensitivity. Setting these sensitivity stages is done with switching means, e.g. a DIL switch. It is of course also possible to adjust sensitivity using a communication interface, for example by means of a PC or that of a network. This then allows the adjusting of a scattered light detector, an entire fire alarm system respectively, by means of just one control center.

Whether the method allows an incremental or a continuous adjustment of the integration time or the pulse width is a function of the monitoring system's boundary conditions. In order to ensure particularly effective and sensitive monitoring, as is necessary for example in clean rooms, scattered light detectors must issue a detection signal at the presence of even the smallest particle quantities in the air, which hence requires a very fine sensitivity adjustment. Besides conventional switches or communication interfaces for PCs or networks, sensitivity adjustments can, of course, also be made wirelessly.

The relationship between temperature and light source emission has already been described in detail above. In the temperature compensation operation, a temperature sensor arranged in the flow path of the carrier medium is hence used for the temperature compensation of the scattered light signal. This means that the temperature of the carrier medium and/or the environment is determined continuously or in pulses in order to be able to adapt the light source which emits light in the scattered light detector. Thus, should a rise in temperature to the carrier medium in the flow path be determined, a direct adjustment of the light source can be made in order to ensure a constant light emission. This temperature compensation is advantageously made by changing the pulse width of the drive current of the light source associated with the scattered light receiver. That means that with a rise in temperature of the carrier medium as detected by the temperature sensor, the pulse width of the light source's drive current is reduced, in consequence of which there is a lesser heating of the light source and thus also the carrier medium. If, instead, a decrease in temperature is determined, the pulse width of the light source's drive current can be increased, which entails a rise in temperature. Yet in all cases, the light source's drive current remains constant.

It is advantageous to filter the scattered light signal differently depending on its slope prior to comparison with preset threshold values, in particular alarm thresholds. In this way, deceptive values can be recognized, eliminated and a false alarm prevented, since only the presence of actual alarm values; i.e. values which are above a given threshold, will lead to an alarm output signal. The amount of time over which the scattered light signal exceeds a threshold value, in particular an alarm threshold, for example, is taken into consideration when doing so. Only once a fixed time interval is reached will an alarm signal then be emitted. The lowpass filtering of the input signal as soon as its slope exceeds a pre-defined threshold furthermore results in a scattered light detector device which has a very good signal-to-noise-ratio, since short, rapid deflections in the input signal, as frequently caused by air pollutants, i.e., small quantities of dust particles in the air flow to be monitored, are not recognized as alarm values.

A further possibility to attain an improved detection algorithm and fewer false alarms with a scattered light detector is to generate a tracked chamber value. This tracked chamber value is averaged from the chamber value of the scattered light detector over a longer period of time and is carried out during the drift compensation operation. The chamber value is the scattered light signal which results when no smoke is present in the scattered light center of the scattered light detector. This scattered light signal is thereby formed from both the detector's own reflection surfaces as well as due to pollutants in the air. Averaging this chamber value in the drift compensation operation over several days (i.e., 2 to 3 days), thus results in a very exact device calibration. This averaged tracked chamber value can be subtracted from the scattered light signal's operating conditions. One is left with a scattered light signal free of errors due to air pollutants, environmental conditions or a detector's own reflectance, etc.

To carry out the above-specified and/or other processing operations, a scattered light detector is presented, the scattered light detector comprising a housing, an inlet opening and an outlet opening in the housing, between which the carrier medium flows along a flow path, a light source, which directs light to a scattered light center lying on the flow path, a scattered light receiver to receive a portion of the light scattered on particles in the scattered light center, and a scattered light signal amplifier to amplify the scattered light signal, the scattered light signal amplifier being configured as an integration amplifier, wherein a filter algorithm operation is provided to filter the scattered light signal based on a slope thereof.

In order to adjust the scattered light receiver's sensitivity, the scattered light detector is provided with switching means. To make switching the device as simple as possible, said switching means can, for example, be a DIL switch.

It is however also possible to configure the switching means as low-priced jumper connections. In order to increase user-friendliness and monitoring possibilities, it makes sense to provide a communication interface, in particular, to a PC or network. This allows the centralized monitoring of a plurality of scattered light detectors, their diagnostics respectively. When doing so, the given communication paths can be either wireless or wired. It therefore makes commensurate sense to provide a switch input for changing the sensitivity of the scattered light receiver.

Arranging a temperature sensor in the flow path of the carrier medium enables the temperature compensation as mentioned above. The arrangement of a flowmeter in the flow path of the carrier medium enables the flow detector to be additionally monitored. For example, it would then be possible to issue a signal upon detecting strong flow fluctuations, since they suggest a malfunctioning of the detector and/or the intake assembly. Configuring the air flow sensor and/or the temperature sensor as thermoelectric components thereby represents an economical and optimally compact possibility of providing the scattered light detector with sensors of high precision.

Additional and/or other aspects and advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
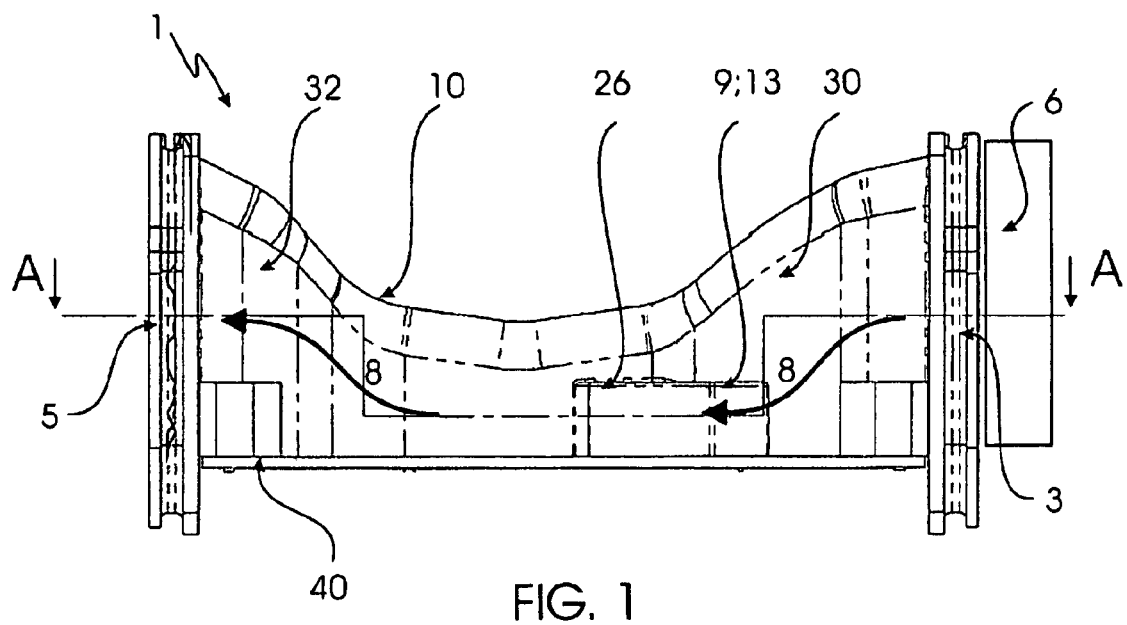
FIG. 1 is a sectional side view of a first embodiment of a scattered light detector.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Embodiments of a scattered light detector 1 used as a component of an aspiration fire alarm system are described below. For reference, the carrier medium is air. This air is suctioned in by a ventilator, as is customary in aspiration fire alarm systems. It is thereby conceivable to arrange the ventilator directly on housing 10 of scattered light detector 1 or yet also within a ventilation duct system external of scattered light detector 1. The methods and devices formulated in the claims are implemented and/or used in the following three embodiments.

FIG. 1 shows a sectional side view of a scattered light detector. The scattered light detector comprises a housing 10 and a circuit board 40 connected thereto. Housing 10 has an inlet opening 3 and an outlet opening 5. Ventilator housing 6, containing a ventilator (not shown), is fixed at the inlet opening 3, said ventilator providing an air flow 8 to flow through detector 1 along flow path 7 (see FIG. 2) from the inlet opening 3 to the outlet opening 5. It is of course also conceivable for the ventilator disposed in ventilator housing 6 to suction air such that an air flow 8' is created which flows in the opposite direction in scattered light detector 1. In order to avoid the incursion of external light from the outside, the scattered light detector 1 exhibits light traps 30 and 32 on both sides thereof. The scattered light detector 1 is further provided with a light source 9 which directs a light cone 20 to a scattered light center 11 (see FIG. 2) lying along flow path 7. The scattered light detector 1 further exhibits a receiver 13 in the form of a photodiode. A screen 26 is provided between photodiode 9 and scattered light receiver 13 which prevents the light radiated by light source 9 from hitting scattered light receiver 13 directly.

Figure 2:
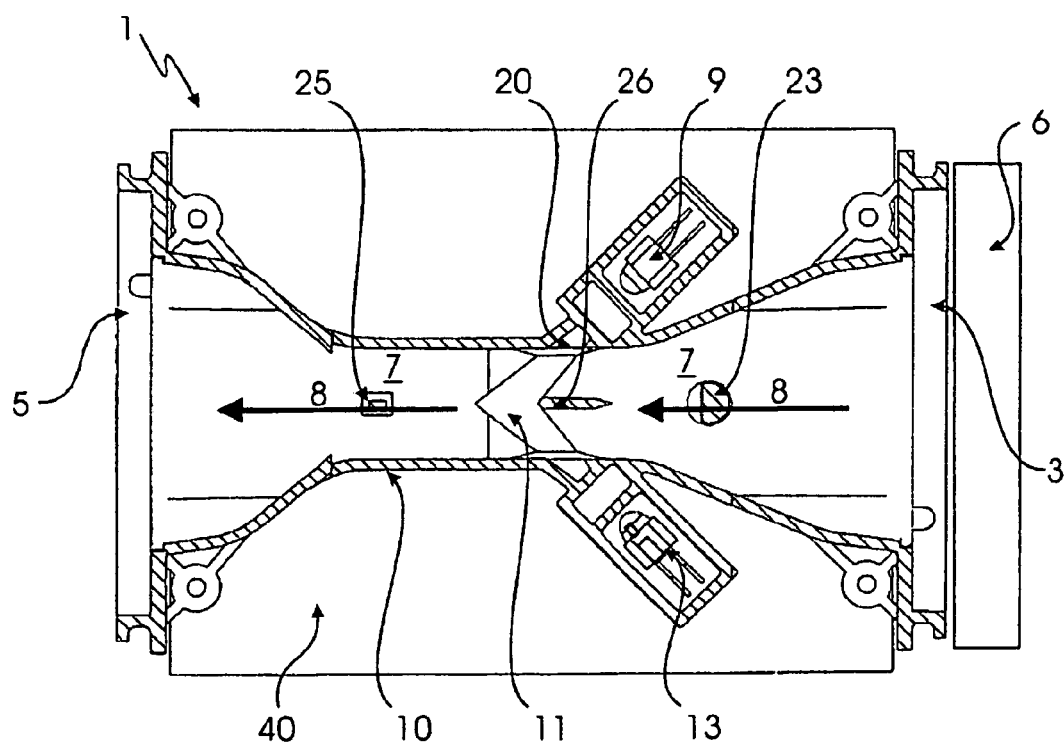
FIG. 2 is a top plan view along the A-A line of the sectioned scattered light detector from the embodiment depicted in FIG. 1.

FIG. 2 shows the first embodiment from FIG. 1 in a sectional top plan view. The orientation to the section corresponds to the A-A intersecting line depicted in FIG. 1. As shown, air, which flows through scattered light detector 1 from inlet opening 3 to outlet opening 5, passes the scattered light center 11. Any fine particles present in air flow 8 thereby reflect the light emitted by light source 9, in this case an LED, onto scattered light receiver 13, which then generates a detection signal once a previously-defined threshold is exceeded. An air flow sensor 25 and a temperature sensor 23 are additionally provided in flow path 7 of the scattered light detector 1. Air flow sensor 25 serves in the assessing of whether a more continuous or some otherwise specific air flow 8 is flowing through scattered light detector 1. In the event of air flow fluctuations, it is, for example, possible to issue a corresponding alarm signal. Temperature sensor 23 monitors the temperature in air flow 8 flowing through scattered light detector 1 along flow path 7 in order to, for example, enable temperature compensation. Temperature compensation is addressed further in FIG. 6.

Figure 3:
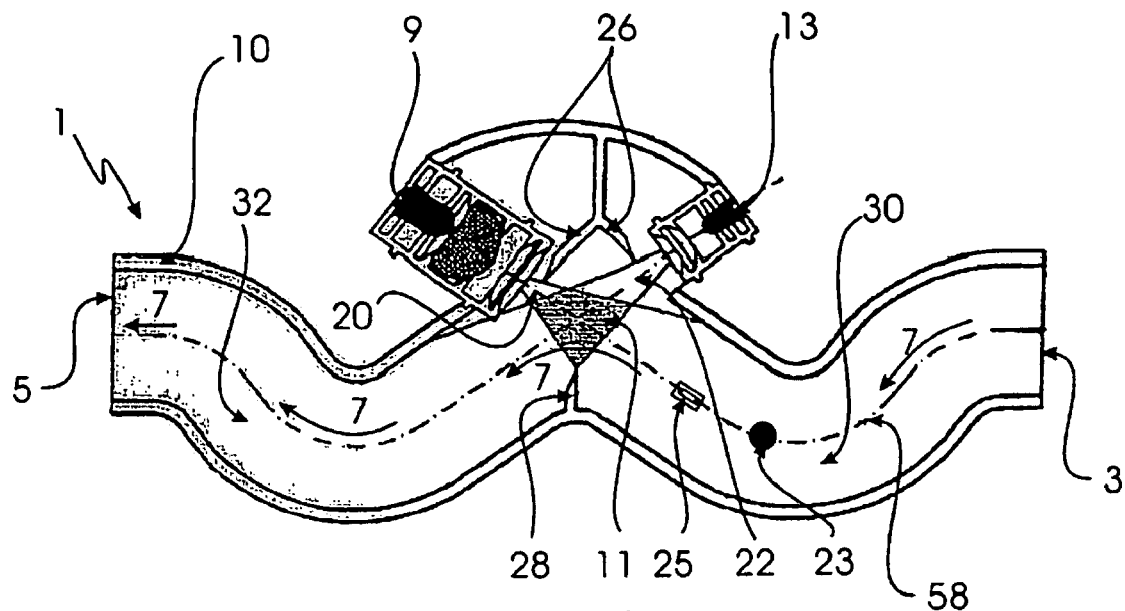
FIG. 3 is a top plan view of a second embodiment of a sectioned scattered light detector.
Figure 4:
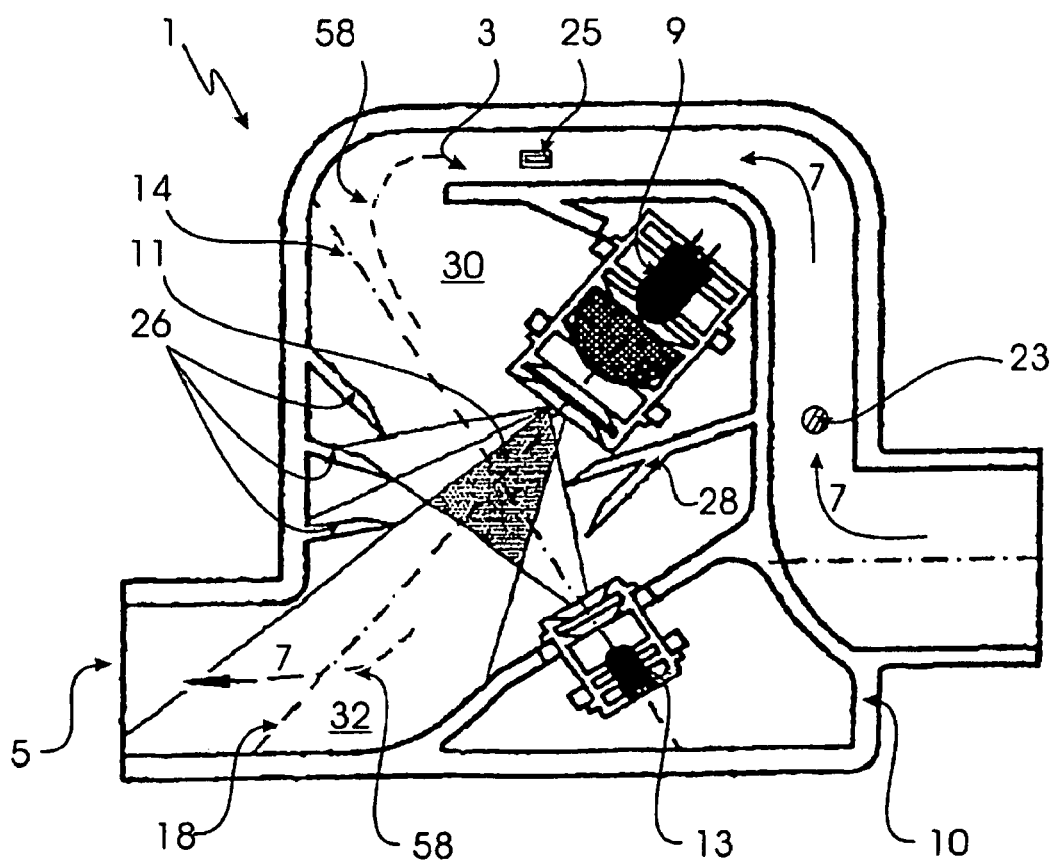
FIG. 4 is a top plan view of a third embodiment of a sectioned scattered light detector.

FIGS. 3 and 4 are both sectional top plan views of second and third embodiments of scattered light detectors. The scattered light detector depicted in each again exhibits the light source 9 and the receiver 13, whereby the light cone 20 of light source 9 and a receiver cone 22 of the scattered light receiver 13 each run crosswise (as in the first embodiment) and over a certain section on a center line 58 of flow path 7. In each case, the flow channel which guides flow path 7 exhibits a bending both in front of scattered light center 11 as well as behind scattered light center 11. The light traps 30 and 32, formed in this manner prevent the intrusion of ambient light from the outside, as in the first embodiment.

The second embodiment, shown in FIG. 3, includes screens 26 and 28, which prevent the reflection of the light emitted from the light source 9 directly onto the scattered light receiver 13. A temperature sensor 23 and an air flow sensor 25 are likewise arranged on the center line 58 of flow path 7 to collect the detection-relevant calibration and monitoring data.

As in the embodiments depicted before, the third embodiment depicted in FIG. 4 of a scattered light detector also exhibits light traps 30 and 32. The center axes 18 and 14 of the light source 9 and the receiver 13, respectively, are aligned such that they run parallel to or along the center line 58 of flow path 7 for a certain segment thereof (e.g., to the two bendings 30 and 32 of flow path 7). In this embodiment as well, screens 26 and 28 are provided to prevent detection of false values. An air flow sensor 25 and a temperature sensor 23 are likewise arranged in the flow channel formed near inlet opening 3. Thus, the temperature and flow rate of an air flow 8 flowing through scattered light detector 1 is checked before it reaches the scattered light center 11.

Several processing operations are used in the scattered light detectors 1, as described above. In more detail, the scattered light signal received by scattered light receiver 13 runs through a calibration operation, a drift compensation operation, a temperature compensation operation, a sensitivity adjustment operation and/or a filter algorithm operation in any order. The calibration operation and drift compensation operation serve in adapting the respective scattered light receiver to, among other things, different carrier media flowing through the flow detector, whereby calibration assumes an air flow 8, as given under normal conditions, at its respective place of use. Obviously a scattered light detector used in office spaces must be calibrated to a different airflow 8 than a scattered light detector used in clean rooms. This is taken into consideration in the calibration and/or drift compensation operation. The difference between these two operations is that in the drift compensation operation, the so-called chamber value, the scattered light signal detected by scattered light receiver 13 if no smoke or similar foreign matter which could trigger an alarm in scattered light center 11 is detected, is averaged over a longer period of time, which usually means two to three days. This so-called tracked chamber value is then subtracted from the detected scattered light signal in order to calibrate scattered light detector 1. Adjusting the temperature of air flow 8 is possible in consequence of the temperature signal received from temperature sensor 23. Here, as noted at the outset, the fact that as the temperature rises, the light output emitted from light source 9 diminishes is taken into consideration. In order to now receive a detected output of scattered light detector 1 independent of temperature, the corresponding adjustment is made in the temperature compensation operation. The scattered light signal detected by scattered light receiver 13 in the different embodiments is additionally filtered differently in a filter algorithm operation. In order to eliminate any possible false signals, it is conceivable to filter the scattered light signal based on its slope prior to comparing it to the preset thresholds which would lead to an alarm signal.

In order to ensure with all three scattered light detectors as exact and sensitive of a monitoring of air flow 8 as possible, the various embodiments exhibit a scattered light amplifier (not shown) to amplify the scattered light signal detected by scattered light receiver 13, for example in the form of an integration amplifier. This integration amplifier enables, for example, by modifying the integration time, a change in the sensitivity of scattered light receiver 1. The greater the integration time selected, the more sensitive the scattered light detector 1 becomes. This change can be made incrementally or continuously.

Figure 5:
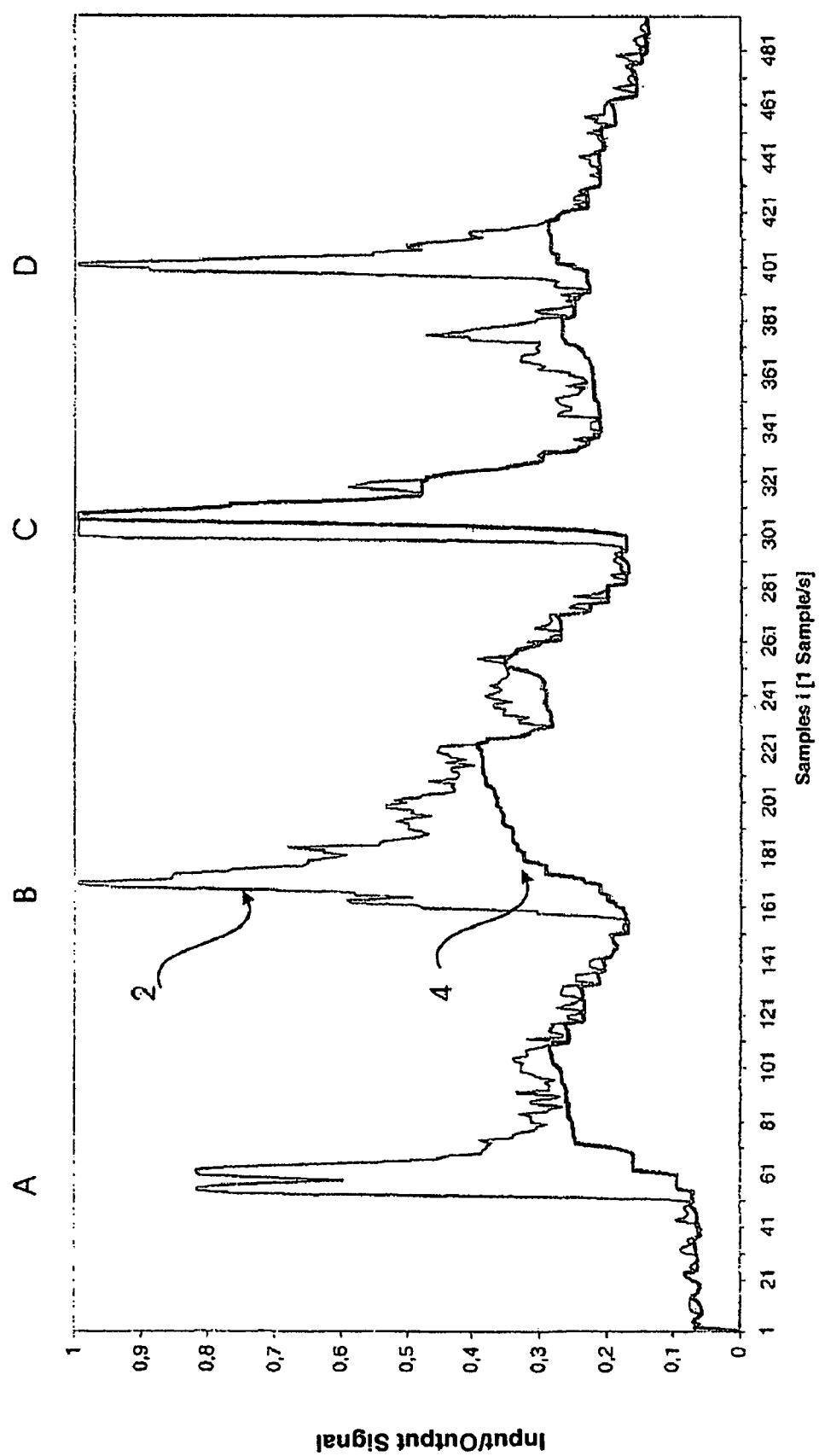
FIG. 5 is an input/output signal graph of a scattered light detector.

FIG. 5 shows a signal input/output graph. Input signal 2 thereby corresponds to an unfiltered signal, as would be detected by scattered light receiver 13 in scattered light detector 1. Output signal 4, in contrast, corresponds to a signal which has already been modified by special filter algorithms. Note is to be made here of the four peak values A, B, C, D in input signal 2, whereby only peak value C exceeds the threshold value of "1" over a longer period of time, based on which an alarm or detection signal will be triggered. In contrast, the so-called deceptive values A, B and D are capped by the filter algorithm and do not lead to an alarm signal. To be noted here is that while false values B and D also exceed the "1" threshold, their exceedance does not last long enough and are thus not recognized as an alarm value by the internal filter and are thus capped. An adapted filter specification can thus yield a scattered light detector which is optimally adapted to environmental and other similar conditions.

Figure 6:
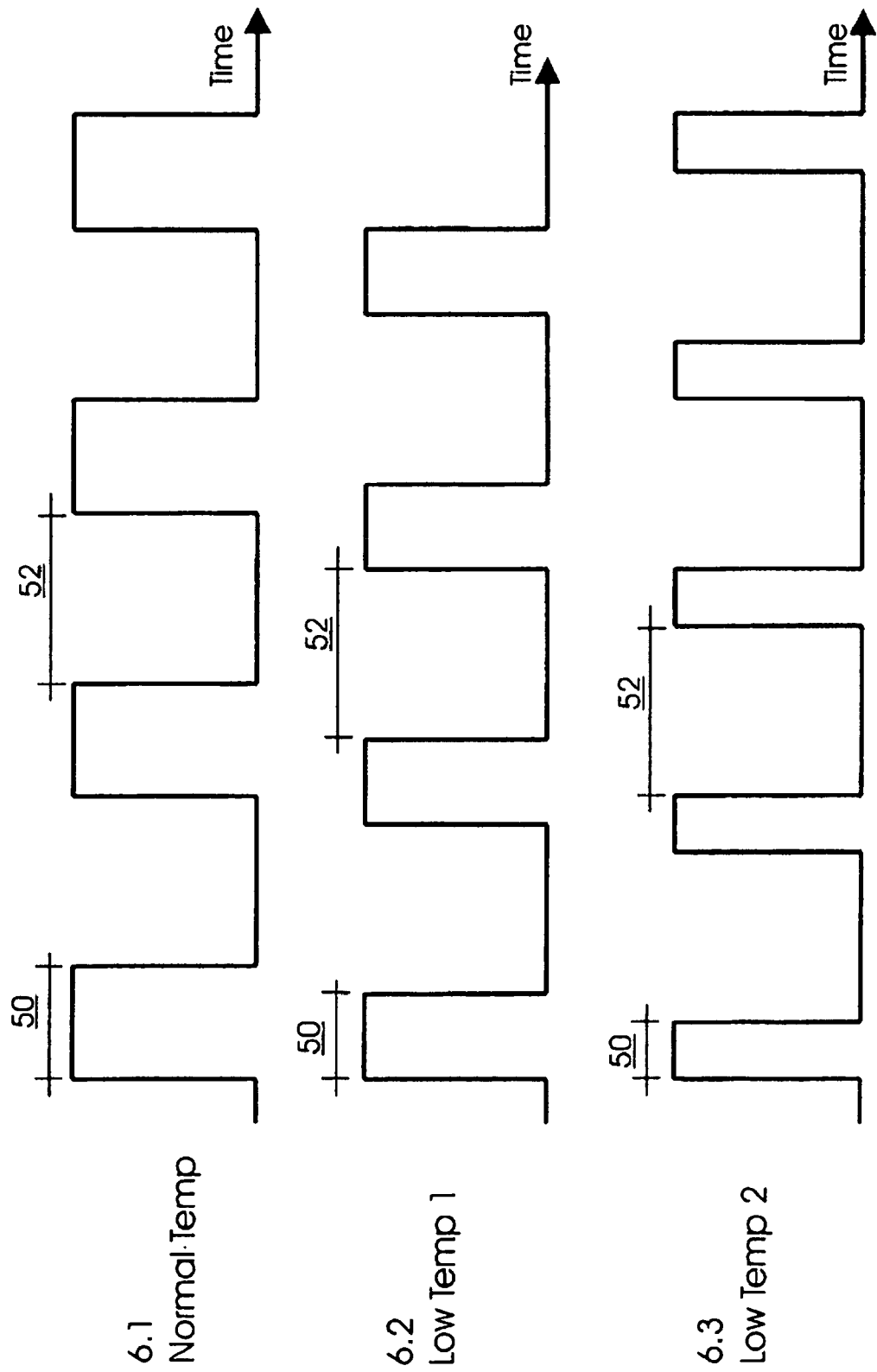
FIG. 6 is a diagram depicting the changes in pulse width for the drive current of a light source in relation to temperature.

FIG. 6 represents possibilities for compensating temperature in the three flow detectors from FIGS. 1 to 3. Shown first in Ill. 6.1 is a diagram of the pulsed operation of light source 9. In normal operation, same exhibits a pulse phase 50 having a pulse width of, for example, three milliseconds, followed by a rest phase 52 of one second. In rest phase 52, light source 9 cools down while in pulse phase 50 it heats up, so that a consistent temperature profile can be expected in the air flow channel under normal conditions. However, should air flow sensor 25 determine a rise in temperature, it is possible, as depicted in Ill. 6.2 and 6.3, to gradually reduce the pulse width of pulse phase 50 in order to effect a lower resulting temperature for light source 9. Changing the pulse width of the light emission—this corresponds to changing the pulse width of the drive current for light source 9—of course also effects a decrease in sensitivity, which can then be compensated accordingly in the sensitivity adjustment step or another calibration step.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A method evaluating a scattered light signal generated by a scattered light receiver when detecting especially fine particles in a carrier medium, comprising running the scattered light signal through a filter algorithm to evaluate the scattered light signal subject to specific filter algorithms, the filter algorithm operation being based on a slope of the scattered light signal.

2. The method according to claim 1, wherein the scattered light signal is run through a calibration operation to calibrate the scattered light signal with a reference signal, a drift compensation operation to adapt the scattered light signal to prevailing environmental conditions over a time period of at least 24 hours, a temperature compensation operation to compensate for the temperature dependency of the radiated light output of a light source, and/or a sensitivity adjusting operation to adapt the scattered light signal to a required sensitivity.

3. The method according to claim 2, wherein the scattered light signal is low-pass filtered when a slope thereof exceeds a pre-defined threshold.

4. The method according to claim 2, wherein a chamber value is averaged over a relatively long period of time in the drift compensation operation to create a tracked chamber value.

5. The method according to claim 2, wherein the barrier medium flows along a flow path and a temperature sensor arranged in the flow path of the carrier medium is used for the temperature compensation in the temperature compensation operation of the scattered light signal.

6. The method according to claim 5, wherein the temperature compensation operation comprises changing a pulse width of a drive current of a light source associated with the scattered light receiver.

7. The method according to claim 2, wherein an integration amplifier acts as a scattered light amplifier, the integration time of the integration amplifier is set in the calibration operation, and wherein the scattered light signal corresponds to a reference signal of a reference indicator.

8. The method according to claim 7, wherein the sensitivity of the scattered light receiver is changed in the sensitivity adjusting operation by changing the integration time in the integration amplifier.

9. The method according to claim 8, wherein the changing of the integration time is incremental or continuous.

10. The method according to claim 2, wherein the sensitivity of the scattered light receiver is changed in the sensitivity adjusting operation by changing a pulse width of a drive current of a light source associated with the scattered light receiver.

11. The method according to claim 10, wherein the changing of the pulse width is incremental or continuous.

12. A scattered light detector comprising:
a housing;
an inlet opening and an outlet opening in the housing, between which a carrier medium flows along a flow path;
a light source which directs light to a scattered light center lying in the flow path;
a scattered light receiver to receive a portion of the light scattered on particles in the scattered light center;
a scattered light signal amplifier to amplify the scattered light signal, the scattered light signal amplifier being configured as an integration amplifier; and
means for providing a filter algorithm operation to filter the scattered Light based on a slope thereof.

13. A scattered light detector according to claim 12, further comprising switching means for setting the sensitivity of the scattered light receiver.

14. A scattered light detector according to claim 12, further comprising a communication interface to communicate with a desktop or a notebook PC.

15. A scattered light detector according to claim 12, further comprising a switch input for changing the sensitivity of the scattered light receiver.

16. A scattered light detector according to claim 12, further comprising a temperature sensor arranged in the flow path of the carrier medium.

17. A scattered light detector according to claim 12, further comprising a flow meter arranged in the flow path of the carrier medium.

18. A scattered light detector according to claim 17, wherein the flow meter comprises a thermoelectric air flow sensor and a thermoelectric temperature sensor.

* * * * *